United States Patent
Ambor et al.

(10) Patent No.: US 8,446,465 B2
(45) Date of Patent: May 21, 2013

(54) SYSTEM AND METHOD FOR DISPLAYING AN IMAGE STREAM CAPTURED IN-VIVO

(75) Inventors: Iddo Ambor, Binyamina (IL); Mordechai Frisch, Moreshet (IL); Eli Horn, Kiryat Motzkin (IL); Michael Skala, Zichron Yaaqov (IL)

(73) Assignee: Given Imaging Ltd., Yoqneam (IL)

( * ) Notice: Subject to any disclaimer, the term of this patent is extended or adjusted under 35 U.S.C. 154(b) by 665 days.

(21) Appl. No.: 12/652,293

(22) Filed: Jan. 5, 2010

(65) Prior Publication Data

US 2011/0164126 A1 Jul. 7, 2011

(51) Int. Cl.
*H04N 7/18* (2006.01)

(52) U.S. Cl.
USPC .......................................................... 348/65

(58) Field of Classification Search
None
See application file for complete search history.

(56) References Cited

U.S. PATENT DOCUMENTS

| | | | |
|---|---|---|---|
| 5,604,531 A | | 2/1997 | Iddan et al. |
| 6,434,569 B1 * | | 8/2002 | Toshimitsu et al. |
| 7,009,634 B2 | | 3/2006 | Iddan et al. |
| 7,215,338 B2 * | | 5/2007 | Horn et al. |
| 2002/0177779 A1 | | 11/2002 | Adler et al. |
| 2005/0075551 A1 | | 4/2005 | Horn et al. |
| 2006/0074275 A1 | | 4/2006 | Davidson et al. |
| 2008/0193139 A1 | | 8/2008 | Bettesh |
| 2008/0244374 A1 * | | 10/2008 | Hattori |
| 2008/0279437 A1 * | | 11/2008 | Hendricks et al. |

OTHER PUBLICATIONS

U.S. Appl. No. 12/282,700, filed May 21, 2009, Radeva et al.

* cited by examiner

*Primary Examiner* — Sath V Perungavoor
*Assistant Examiner* — Kate Luo
(74) *Attorney, Agent, or Firm* — Pearl Cohne Zedek Latzer, LLP (57) ABSTRACT

A system and method may allow automatic display of unviewed images of an image stream, which may be produced by an ingestible capsule. A set of images acquired by an in-vivo device disposed within a body lumen is received by a receiver or workstation, and a portion of the set of images is selected for display as an image stream. The selected portion of images is displayed as a first image stream, and a complementary portion of the set of images is displayed as a second image stream. The complementary portion includes unselected images from the set of images, and/or images which are indicated as unviewed images. A graphical user interface is provided for selecting a viewing mode which is determined based on previously viewed images and users' review history.

19 Claims, 4 Drawing Sheets

SYSTEM AND METHOD FOR DISPLAYING AN IMAGE STREAM CAPTURED IN-VIVO

FIELD OF THE INVENTION

The present invention relates to a method and system for displaying and viewing an image stream captured in-vivo. More specifically, the present invention relates to systems and methods for viewing an in-vivo image stream which has been previously viewed or partially viewed.

BACKGROUND OF THE INVENTION

When viewing a movie, for example an image stream which may be used for medical diagnosis, a viewer may desire to view certain portions or frames, or may wish to view a short preview, summarizing specific frames and skipping others, for example, according to one or more pre-defined criteria.

For example, an in-vivo imager system which is carried by an ingestible capsule may be used to image lumens within a patient. The imager system captures and transmits, for example, images of the GI tract to an external recording device while the capsule passes through the GI lumen. Such an in-vivo imaging system provides a platform from which moving or still images of a lumen may be viewed. Large numbers of images, for example 50,000 or 100,000 images, may be collected for viewing. The images may be combined in sequence, and an image stream of, for example, more than 120 minutes in length, may be presented to the user. A user, e.g. a physician, may want to view a summary of the entire capture length, thus reducing viewing time. In some cases, the user may want to view the complete movie or a substantial portion of the movie.

SUMMARY OF THE INVENTION

An exemplary embodiment of the present invention provides a system and method for viewing an image stream, the image stream preferably being produced by an in-vivo imaging device such as an ingestible or swallowable capsule. A workstation accepts images and displays the images as an image stream on a display or monitor. A user may select a viewing method to view an image stream or a portion thereof, and may receive an indication of the images that had already been viewed, for example in the current review session and/or in previous review sessions.

The image stream may be edited and reduced, or a stream to be viewed may be selected for initial viewing or preview, using editing methods which may include any number of methods based on pre-determined frame selection and frame skipping, or methods based on algorithmic recognition of pre-determined criteria, e.g. images pertaining to a known symptom, such as bleeding and/or ulcers, etc. An edited image stream may be viewed by several users.

A complementary image stream may be generated and displayed according to embodiments of the present invention. A set of images acquired by an in-vivo device disposed within a body lumen may be received. A portion of the set of images may be selected for display as an image stream. In one embodiment, the selection may be based on at least one predetermined criterion. The selected portion of images may be displayed as a first image stream, and a complementary portion of the set of images may be displayed as a second image stream. The complementary portion may include unselected images (images not previously selected) from the set of images.

A method for displaying a complementary view of an image stream is provided according to one embodiment of the present invention. A set of images acquired by an in-vivo device disposed within a body lumen may be received and stored. At least a portion of the set of images may be displayed to a user as an image stream. A review descriptor, being or including at least an indication that the image has been viewed by a user, may be associated with every image which has been displayed. The review descriptor may be stored, for example along with other image-related information, and a complementary image stream may be generated based on the review descriptors. According to one embodiment, the complementary image stream may include images from the set of images which are indicated as unviewed based on the review descriptor. The complementary image stream may be displayed to a user, for example upon a user's request.

BRIEF DESCRIPTION OF THE DRAWINGS

The principles and operation of the system and method according to the present invention may be better understood with reference to the drawings, and the following description, it being understood that these drawings are given for illustrative purposes only and are not meant to be limiting, wherein.

It will be appreciated that for simplicity and clarity of illustration, elements shown in the figures have not necessarily been drawn to scale. For example, the dimensions and/or aspect ratio of some of the elements may be exaggerated relative to other elements for clarity. Further, where considered appropriate, reference numerals may be repeated among the figures to indicate corresponding or analogous elements throughout the serial views.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. Such apparatuses may be specially constructed for the desired purposes, or may comprise general purpose computers selectively activated or reconfigured by a computer program stored in the computers. Such computer programs may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. It will be appreciated that a variety of programming languages may be used to implement the teachings of the invention as described herein.

Some embodiments of the present invention are directed to a typically swallowable in-vivo device, such as an autonomous swallowable capsule. Other embodiments need not be swallowable or autonomous, and may have other shapes or configurations. Devices according to embodiments of the present invention, including imaging, receiving, processing, storage and/or display units suitable for use with embodiments of the present invention, may be similar to embodiments described in US Patent Application Publication Number 2006/0074275, entitled "SYSTEM AND METHOD FOR EDITING AN IMAGE STREAM CAPTURED IN-VIVO", U.S. Pat. No. 5,604,531 to Iddan et al., entitled "In-vivo Video Camera System", and/or in U.S. Pat. No. 7,009,634 to Iddan et al., entitled "Device for In-Vivo Imaging", all of which are hereby incorporated by reference in their entirety. Of course, devices and systems as described herein may have other configurations and other sets of components. Devices, systems and methods according to some embodiments of the present invention, may be similar to or incorporate embodiments described in US Patent Application Publication Number 2008/0193139, entitled "TWO-WAY COMMUNICATION IN AN AUTONOMOUS IN VIVO DEVICE", incorporated by reference herein in its entirety, which discloses an autonomous in-vivo sensing device that includes an in-vivo transceiver to both transmit wireless signals to for example an external receiver, and to receive wireless signals from for example an external transmitter. Devices, systems and methods according to some embodiments of the present invention, may be similar to the commercial PillCam® SB2 or PillCam® Colon capsules and the associated data recorders and RAPID® workstation of the common assignee. The 2008/0193139 application further discloses that wireless signals received by the in-vivo transceiver may be or may include command or control signals that may activate, de-activate or alter an operational state of one or more functions of the in-vivo device. The wireless signals transmitted by the in-vivo transceiver may be or include sensory data such as for example image data that may be collected by the in-vivo sensing device.

Figure 1A:
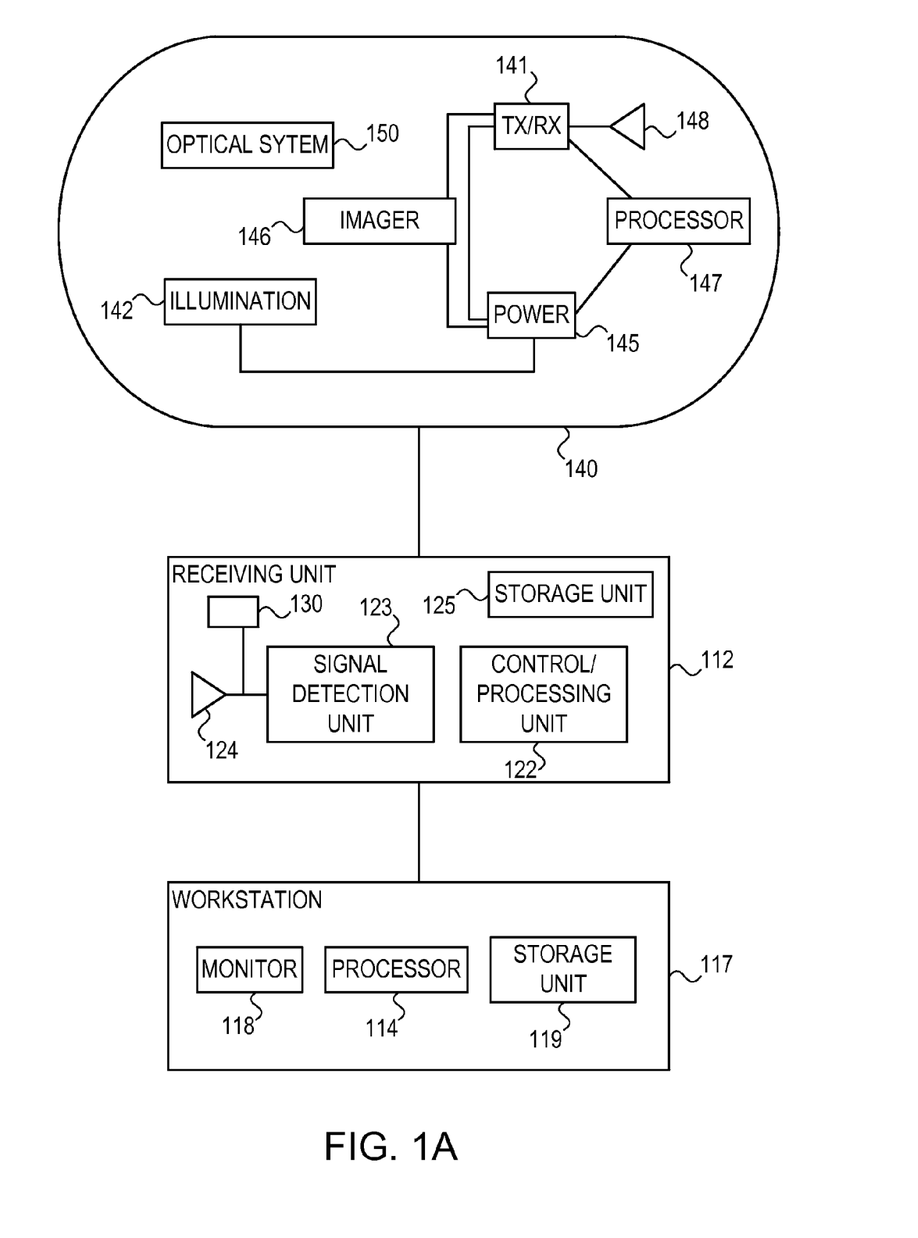
FIG. 1A shows a schematic diagram of an in-vivo imaging system according to an embodiment of the present invention.

Reference is made to FIG. 1A, which schematically illustrates an in-vivo system in accordance with some embodiments of the present invention. One or more components of the system may be used in conjunction with, or may be operatively associated with, the devices and/or components described herein or other in-vivo devices in accordance with embodiments of the invention.

In some embodiments, the system may include a device 140 having a sensor, e.g., an imager 146, one or more illumination sources 142, a power source 145, and a transmitter or transceiver 141. In some embodiments, device 140 may be implemented using a swallowable capsule, but other sorts of devices or suitable implementations may be used.

Receiver/recorder 112 may include a receiver or transceiver 130 to communicate with device 140, e.g., to send control data to device 140 and to periodically receive image, telemetry and device parameter data from device 140. In some embodiments, for example in the case one-way communication is used, device 140 may include a transmitter and receiver/recorder 112 may include a receiver.) Receiver/recorder 112 may in some embodiments be a portable device worn on or carried by the patient, but in other embodiments may be for example combined with workstation 117. A workstation 117 (e.g., a computer or a computing platform) may include a storage unit 119 (which may be or include for example one or more of a memory, a database, or other computer readable storage medium), a processor 114, and a display or monitor 118.

Transceiver 141 may operate using radio waves; but in some embodiments, such as those where device 140 is or is included within an endoscope, transceiver 141 may transmit/receive data via, for example, wire, optical fiber and/or other suitable methods. Other known methods of wireless transmission may be used. Transceiver 141 may include, for example, a transmitter module or sub-unit and a receiver module or sub-unit, or an integrated transceiver or transmitter-receiver. In one embodiment, transceiver 141 includes at least a modulator for receiving an image signal from the sensor 146, a radio frequency (RF) amplifier, an impedance matcher and an antenna 148. The modulator converts the input image signal having a cutoff frequency f0 of less than 5 MHz to an RF signal having a carrier frequency fr, typically in the range of 1 GHz. While in one embodiment, the signal is an analog signal, the modulating signal may be digital rather than analog. The carrier frequency may be in other bands, e.g., a 400 MHz band. The modulated RF signal has a bandwidth of ft. The impedance matcher may match the impedance of the circuit to that of the antenna. Other transceivers or arrangements of transceiver components may be used. For example, alternate embodiments may not include a matched antenna or may include a transceiver without a matching circuit. In alternate embodiments, device 140 may have different configurations and include other sets of components. Other frequencies may be used. In yet further embodiments, sensors other than image sensors may be used, such as pH meters, temperature sensors, pressure sensors, etc. and input RF signals other than image signals may be used.

Transceiver 141 may send different types of signals, including for example telemetry signals, image signals and beacon signals. Other types of signals may be transmitted by transceiver 141. Information sent from device 140 may include information sensed by sensors in the device such as images, pH, temperature, location and pressure. Information sent from device 140 may include telemetry information, regarding the capsule identification number (ID), time counter, image type data and the status of components in the device, such as current image capturing mode or frame rate of the imager, different allowable frame rates, power usage for capturing each individual image frame or a group of image frames, power usage for each allowable frame rate, remaining power of the device power source, amount of energy reserve needed to capture image frames until complete passage of the device through a body passage at a minimal frame rate. The signals may be sent separately or as part as a larger frame, for example a frame including both telemetry-type and image-type signals.

Embodiments of device 140 may be autonomous and self-contained or may be controllable capsules (e.g., magnetically maneuvered). For example, device 140 may be a capsule or other unit where all the components are substantially contained within a container or shell, and where device 140 does not require any wires or cables to, for example, receive power or transmit information. In some embodiments, device 140 may be autonomous and non-remote-controllable; in another embodiment, device 140 may be partially or entirely remote-controllable.

In some embodiments, device 140 may include an in-vivo video camera, for example, imager 146, which may capture and transmit images of, for example, the GI tract while device 140 passes through the GI lumen. Other lumens and/or body cavities may be imaged and/or sensed by device 140. In some embodiments, imager 146 may include, for example, a Charge Coupled Device (CCD) camera or imager, a Complementary Metal Oxide Semiconductor (CMOS) camera or imager, a digital camera, a stills camera, a video camera, or other suitable imagers, cameras, or image acquisition components.

In some embodiments, imager 146 may be operationally connected to transmitter or transceiver 141. Transceiver 141 may transmit images to, for example, external transceiver or receiver/recorder 112 (e.g., through one or more antennas), which may send the data to workstation 117, processor 114 and/or to storage unit 119. Transceiver 141 may also include control capability, although control capability may be included in a separate component, e.g., processor 147. Transceiver 141 may include any suitable transmitter able to transmit image data, other sensed data, and/or other data (e.g., control data, beacon signal, etc.) to a receiving device. Transceiver 141 may also be capable of receiving signals/commands, for example from an external transceiver. For example, in some embodiments, transceiver 141 may include an ultra low power Radio Frequency (RF) high bandwidth transmitter, possibly provided in Chip Scale Package (CSP).

In some embodiments, transceiver 141 may transmit/receive via antenna 148. Transceiver 141 and/or another unit in device 140, e.g., a controller or processor 147, may include control capability, for example, one or more control modules, processing module, circuitry and/or functionality for controlling device 140, for controlling the frame capture rate or settings of device 140, and/or for performing control operations or processing operations within device 140. According to some embodiments, transceiver 141 may include a receiver which may receive signals (e.g., from outside the patient's body), for example, through antenna 148 or through a different antenna or receiving element. According to some embodiments, signals or data may be received by a separate receiving device in device 140.

Power source 145 may include one or more batteries or power cells. For example, power source 145 may include silver oxide batteries, lithium batteries, other suitable electrochemical cells having a high energy density, or the like. Other suitable power sources may be used. For example, power source 145 may receive power or energy from an external power source (e.g., an electromagnetic field generator), which may be used to transmit power or energy to in-vivo device 140.

In some embodiments, power source 145 may be internal to device 140, and/or may not require coupling to an external power source, e.g., to receive power. Power source 145 may provide power to one or more components of device 140 continuously, substantially continuously, or in a non-discrete manner or timing, or in a periodic manner such as each time a frame is captured, an intermittent manner, or an otherwise non-continuous manner. In some embodiments, power source 145 may provide power to one or more components of device 140, for example, not necessarily upon-demand, or not necessarily upon a triggering event or an external activation or external excitement.

Transceiver 141 may include a processing unit, processor or controller, for example, to process signals and/or data generated by imager 146. In another embodiment, the processing unit may be implemented using a separate component within device 140, e.g., controller or processor 147, or may be implemented as an integral part of imager 146, transceiver 141, or another component, or may not be needed. The processing unit may include, for example, a Central Processing Unit (CPU), a Digital Signal Processor (DSP), a microprocessor, a controller, a chip, a microchip, a controller, circuitry, an Integrated Circuit (IC), an Application-Specific Integrated Circuit (ASIC), or any other suitable multi-purpose or specific processor, controller, circuitry or circuit. In some embodiments, for example, the processing unit or controller may be embedded in or integrated with transceiver 141, and may be implemented, for example, using an ASIC.

In some embodiments, imager 146 may acquire in-vivo images in a discrete or periodic manner, or in an intermittent manner, or an otherwise non-continuous manner, for example, at an interval according to a variable one of a plurality of frame capture rates. An imaging or image capturing procedure may include the time period during which the imager 146 is capturing images and the transceiver 141 is transmitting the image data to the receiving unit 112. Commands may be received by the device 140 from an external control unit which may be a separate unit located outside of the patient's body or may be integrated, for example with the receiving unit 112. The external control unit may be, for example, the control/processing unit 122 integrated within receiving unit 112.

In some embodiments, device 140 may include one or more illumination sources 142, for example one or more Light Emitting Diodes (LEDs), "white LEDs", or other suitable light sources. Illumination sources 142 may, for example, illuminate a body lumen or cavity being imaged and/or sensed. An optical system 150, including, for example, one or more optical elements, such as one or more lenses or composite lens assemblies, one or more suitable optical filters, or any other suitable optical elements, may optionally be included in device 140 and may aid in focusing reflected light onto imager 146, focusing illuminating light, and/or performing other light processing operations.

In some embodiments, the components of device 140 may be enclosed within a housing or shell, e.g., capsule-shaped, oval, or having other suitable shapes. The housing or shell may be substantially transparent, and/or may include one or more portions, windows or domes that may be substantially transparent. For example, one or more illumination source(s) 142 within device 140 may illuminate a body lumen through a transparent, window or dome; and light reflected from the body lumen may enter the device 140, for example, through the same transparent or portion, window or dome, or, optionally, through another transparent portion, window or dome, and may be received by optical system 150 and/or imager 146. In some embodiments, for example, optical system 150 and/or imager 146 may receive light, reflected from a body lumen, through the same window or dome through which illumination source(s) 142 illuminate the body lumen.

According to one embodiment, while device 140 traverses a patient's GI tract, the device 140 transmits image and possibly other data to components located outside the patient's body, which receive and process the data. Typically, receiving unit 112 is located outside the patient's body in one or more locations. The receiving unit 112 may typically include, or be operatively associated with, for example, one or more antennas, sensors, or an antenna array 124, for receiving and/or transmitting signals from/to device 140. Receiving unit 112 typically includes an image receiver storage unit 125, e.g. a memory and/or mass storage unit such as a hard drive. According to one embodiment, the image receiver 112 and image receiver storage unit 125 are small and portable, and are typically worn on the patient's body (or located in close proximity to the patient's body) during recording of the images. The receiving unit 112 may include display 126, for example an LCD (Liquid Crystal Display), which may be used to provide instructions for the patient during and/or before the imaging procedure, to view images captured by device 140 (for example in real time, while the image frames are captured or with a minimal delay). A user may select to view specific images on receiving unit 112, and may mark or annotate them, using, for example, user interface input mechanism such as buttons which may be provided on receiving unit 112.

The receiving unit 112 may include, or be operatively associated with a signal detection unit 123, which may detect signals transmitted from, for example, device 140. The signal detection unit 123 may be coupled or included in the antenna or antenna array 124.

In some embodiments, device 140 may communicate with an external receiving and display system (e.g., workstation 117 or monitor 118) which may provide different display modes of image data, and/or other data (e.g. control, location, other sensed data such pH). Other embodiments may have other configurations and capabilities. For example, components may be distributed over multiple sites or units, and control information or other information may be received from an external source.

Processor 114 and processor 122 may include processing units, processors or controllers. The processing units may include, for example, a CPU, a DSP, a microprocessor, a controller, a chip, a microchip, a controller, circuitry, an IC, an ASIC, or any other suitable multi-purpose or specific processor, controller, circuitry or circuit.

According to one embodiment, the in-vivo imaging system collects a series of still images as device 140 traverses the GI tract. The images may be later presented as, for example, a stream of images or an image stream of the traverse of the GI tract. The in-vivo imaging system may collect a large volume of data, as device 140 may take several hours to traverse the GI tract, and may record images at a rate of, for example, 2-72 images every second, resulting in the recordation of thousands of images during a single imaging procedure. The image recordation rate (or frame capture rate) may be varied as the device progresses.

Preferably, the image data recorded and transmitted by the device 140 is digital color image data, although in alternate embodiments other image formats may be used. In an exemplary embodiment, each frame of image data includes 256 rows of 256 pixels each, each pixel including bytes for color and brightness, according to known methods. For example, in each pixel, color may be represented by a mosaic of four sub-pixels, each sub-pixel corresponding to primaries such as red, green, or blue (where one primary is represented twice). The brightness of the overall pixel is recorded by a one byte (i.e., 0-255) brightness value. According to one embodiment, images are stored sequentially in data processor storage unit 119. The stored data may be comprised of one or more pixel properties, including color and brightness.

Data processor 114 may analyze the data received via external receiver/recorder 112 from device 140, and may be in communication with storage unit 119, e.g., transferring image frame data, control data, location data, and other data to and from storage unit 119. Storage unit 119 may include, for example, a database and/or may use other storage methods. Data processor 114 may provide the analyzed data to monitor 118, where one or more users (e.g., physicians, nurses) may view or otherwise use the data, for example review it using different viewing or display modes. Data processor 114 may also be connected to one or more user input interfaces such as a keyboard and a mouse.

Figure 1B:
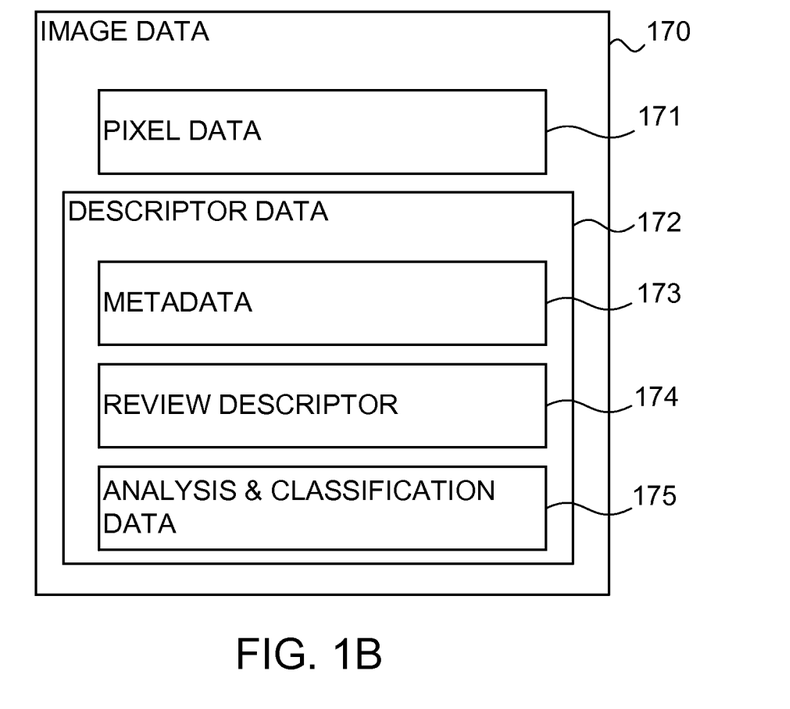
FIG. 1B illustrates an image data set according to an embodiment of the present invention.

In an exemplary embodiment, the image stream may be stored as a series of images in storage unit 119, along with descriptor data which may include image-related data as for example shown in FIG. 1B. In some embodiments, the image pixel data which may include the image itself, may be stored for example in an image database, which may be part of storage unit 119. In some embodiments, a separate storage method or unit may be used for the descriptor data, e.g. metadata and user review data, however other embodiments may include all image data 170 in the same storage unit. The image data 170 may be stored in various combinations; for example, pixel data 171 and descriptor data 172 may be stored in the same database or in separate (e.g. remote) databases or storage units. Preferably, if separate storage units are used, an entry in a pixel database corresponds to an entry in an image descriptor database. For example, an entry in pixel database may include a link, such as a pointer or a database reference key, which connects it to the corresponding entry in the descriptor database. The link may include, for example, the relative time the image was captured or an image frame index number. In alternate embodiments, no such links are needed, as the image data and descriptor data may be stored in the same database or storage unit. Descriptor data 172 may include, for example, information about the display time of the image, for example per user or user group, a total accumulated time that the image was displayed, and/or an indication whether the image has been displayed or not. In some embodiments, image descriptor information may be stored for one or more images of an image stream, or for images in an edited image stream, for example image streams including merged images or a reduced number of images. In alternate embodiments other information describing the image may be stored in the image descriptor data 172 and may be used to carry out embodiments of the present invention.

In some embodiments, data processor 114 may be configured for real time processing and viewing, and/or for post processing to be performed and/or viewed at a later time. In the case that control capability (e.g., delay, timing, etc) is external to device 140, a suitable external device (such as, for example, data processor 114 or external receiver/recorder 112 having a transmitter or transceiver) may transmit one or more control signals to device 140.

For example, processor 114 may mark each image from a specific set of images which has been viewed by a user, for example upon an initial display of an image on monitor 118 or on a different display device. Processor 114 may calculate the complementary set of images for the specific set of images being viewed. If a user has been viewing a subset A of the complete set of images S, the complementary set of images $A^C$ (the relative complement set) may include all the images which have not been marked at a given point in time, e.g. the time that the user selects to view the complementary mode. For example, a user may be viewing the complete set of images S. The user may be viewing certain portions, and may for example skip some images and linger on others. All viewed images may be marked or otherwise indicated that they have been viewed by the user, for example the marking of an image may be performed as the image is being displayed, or substantially immediately thereafter. After some time, for example 30 minutes, the user may decide to switch viewing modes, and review the complementary set which includes all unviewed (e.g. unmarked) images.

The set of unviewed images may be calculated (e.g. by processor 114 or processing unit 122) substantially at the moment the user requested the complementary view mode. After viewing the complementary movie for a few minutes, the user may choose to revert back to the complete set of images (e.g., the normal view). At this time, the complementary set of images may be updated, e.g. images which the user viewed in the complementary viewing mode may be marked as viewed, and may be removed from the set of unviewed images. In other embodiments, the complementary set of images may be calculated on the fly, e.g. while the user is reviewing the complementary movie, the set of images marked as unviewed may be constantly updated as each previously unviewed image is marked as a viewed image. The processor may select for display only images which are indicated as unviewed at the time they are intended to be displayed. In some embodiments, the images may be displayed according to the chronological order of capturing (e.g., according to a timestamp of the image). In other embodiments, the images may be displayed according to other sorting methods. For example, images may be sorted according to the number of users who have reviewed them, or according to the total accumulated time they had been reviewed/displayed.

Monitor 118 may include, for example, one or more screens, monitors, or suitable display units. Monitor 118, for example, may display one or more images or a stream of images captured and/or transmitted by device 140, e.g., images of the GI tract or of other imaged body lumen or cavity. Additionally or alternatively, monitor 118 may display, for example, image descriptor data 172, which may include, but is not limited to, information about the display/review history of one or more images and one or more users, control data, location or position data (e.g., data describing or indicating the location or the relative location of device 140), orientation data, and various other suitable data. In some embodiments, for example, both an image and data relating to the display history of the image may be presented using monitor 118 and/or may be stored using storage unit 119. Other systems and methods of storing and/or displaying collected image data and/or other data may be used.

The image data collected and stored may be stored indefinitely, transferred to other locations, or manipulated or analyzed. A health professional may use the images to diagnose pathological conditions of for example the GI tract and, in addition, the system may provide information about the location of these pathologies. While using a system where the storage unit 119 first collects data and then transfers data to processor 114, the image data may not viewed in real time, other configurations allow for real time viewing. In one embodiment, while the images are being viewed in real time, for example on an LCD (Liquid Crystal Display) of receiver 112, the displayed images may be marked or otherwise indicated as 'viewed' or 'displayed' images. For example, an image review descriptor may indicate or may be associated with each image which has been viewed. A health care professional may be interested in reviewing the rest of the images in the stream, e.g. only images which have not been previously viewed by him or by another user (e.g., images not selected for a first viewing), e.g. to save time. The indication of the images as "viewed images" may be used later by processor 114, for example to generate a display of the unviewed images upon the user's request.

The stream of images may include, for example, a subset of images selected according to one or more predetermined criterions from the set of images captured by device 140. In other examples, the stream of images may include a subset of images from the image stream selected according to a user's preference or viewing habit. In one embodiment, a user may be interested in knowing which images have already been viewed, possibly by the user himself or by one or more different users. Monitor 118 may provide different viewing/display options, for example to allow a user to view only images which have not been reviewed yet by another, or to allow a user to see in a graphical representation which images from the stream have already been viewed.

In one embodiment, display modes may be determined on-the-fly, for example per user's request, or according to a user group which may be determined on-the-fly. The display modes may include viewing different subsets of the image stream captured by device 140. One display mode may include a summary movie or a reduced stream of images, for example a preview movie which may include clinically 'interesting' images selected from the original (e.g. complete) set of captured images, for example automatically selected from the image stream by processor 114 and/or processor 122, or marked as clinically 'interesting' by the in vivo device. Another display mode may include a different subset of images, for example all the images from the set of captured images which were not selected as 'interesting' images. Other display modes may include viewing all images, and/or viewing a reduced movie of merged images based on image similarity. In some embodiments, the images reviewed by a user may be automatically marked or indicated as "viewed images", for example using an indicator or review descriptor which may be associated to the image or to a group of images and stored in storage unit 119.

Typically, device 140 may transmit image information in discrete portions. Each portion may typically correspond to an image or a frame; other suitable transmission methods may be used. For example, in some embodiments, device 140 may capture and/or acquire an image at one of a plurality, e.g., three, four, ten or a hundred, different frame capture rates, and may transmit the image data to the external receiving unit 112. Other constant and/or variable capture rates and/or transmission rates may be used.

Monitor 118 may present the image data, preferably in the form of still and moving images, and in addition may present other information. In an exemplary embodiment, such additional information may include, but is not limited to, absolute display time elapsed for the current image being shown per a specific user or reviewer, accumulated display time elapsed for the current image being shown, date of review (e.g., per session), number of different sessions that the movie had been reviewed in, and summary information. Absolute display time elapsed for the current image being shown per a specific user or reviewer may be, for example, the amount of time that elapsed between the moment the current image was displayed for review by a certain user and the moment that the image was no longer being displayed on monitor 118, for example if it was replaced by another image. Accumulated display time elapsed may be the total amount of time that the image was displayed on monitor 118 (and/or on different monitors or display units such as display 126) by all reviewers.

In further embodiments the date of review per image (or per a group or a set of images) may be stored in the review descriptor 174 of image descriptor 172 (shown in FIG. 1B) and may be presented to the reviewer, for example upon request or automatically while viewing the image, for example in a specific viewing mode. In an exemplary embodiment, the various categories of information may be displayed in different portions of the display or in windows. In some embodiments, the review session history information may be stored may be stored separately from the image data 170, in storage unit 119 or in other storage units, and may be linked to image data 170 for example by a pointer or based on a database key value such as the frame index number or the time that the frame was captured. Such information may include, but is not limited to, the total length of the review session, the name and title of the reviewer, the date and time of review, the percentage of images that were reviewed during the session, the segments or organs which were partially or completely reviewed during the session, the image streams or subsets of image streams which were reviewed, etc. Typically, a dedicated review descriptor 174 may be associated with every image, or with every reviewed image, such that each image has its own review descriptor. However, in some embodiments, a single review descriptor 174 may be associated with more than one image, for example with multiple images which had been viewed by a user in a single review session.

The different viewing modes may allow the image streams to be frozen to view one frame, speeded up, or reversed. According to one embodiment sections may be skipped automatically or by a user according to one or more predefined criteria, which may be applied to the image stream.

When used herein, "predefined criteria" and its derivatives may indicate any kind of logical algorithms/method or rules such as rules that select one or more images, anomalous or "interesting" images (e.g. images which are a deviation from normal images or from common images encountered, for example, in capsule endoscopy video stream of healthy patients) according to one or more parameters. The parameters may be numerically based, as in selecting a predefined number of images from a predetermined segment or organ of the GI tract, for example selecting 1000 images from the small bowel and 15,000 images from the colon. In other embodiments, one in every hundred or two hundred images generated for viewing may be selected, to ensure a smooth flow of the reduced movie and to make it easier to follow changes in the images. According to some embodiments the parameters may be image quality based, for example selecting the most qualitative or "interesting" image from each group of images. Other methods of editing may be based on different criteria such as logic scanning for a certain predefined area or image in an image database, such as medical diagnosis automatic scan for internal bleeding based on color differentiation within the image or percentage of resemblance to a pre-existing image in a database, which may be similar to that described in US Patent Application Publication no. 2002/0177779 titled "METHOD AND SYSTEM FOR DETECTING COLORIMETRIC ABNORMALITIES IN-VIVO", which is incorporated by reference in its entirety.

According to some embodiments of the present invention, the user can also define and create a viewing mode or method according to specific needs, and choose how many or which specific frames to display. A specific time frame can be set for each body area, for example viewing every n'th image generated from the esophagus (e.g., every third image) and every m'th (e.g. $30^{th}$) image generated from the stomach lumen. Additionally, according to some embodiments, a number of editing/viewing methods may be combined and employed, for example scanning for suspected bleeding areas and displaying every third frame of the scads results.

Reference is now made to FIG. 1B, which illustrates an image data set, according to an embodiment of the present invention. The image data set 170 may include different data types, for example pixel data 171 and descriptor data 172. The descriptor data 172 may include sub-types such as metadata 173, review descriptor 174 and analysis/classification data 175. Each data type or sub-type may be associated to the image at different times, for example the pixel data 171 and metadata 173 may include information captured by device 140, while the review descriptor 174 may be associated to an image after a first display of the image to a user. The analysis/classification data 175 may be associated to the image after digital processing of the image in the workstation 117. In some embodiments, some of the data types or sub-types may remain void or null, for example in some of the images, or in all images of the data stream. The pixel data 171 may include the in vivo raw image as captured by device 140.

Metadata 173 may include, for example, data regarding the captured image such as the capture frame rate, the image gain and illumination levels used by the device 140 for capturing the image, the frame index number, the time and date of capturing the image, the anatomical location of the device 140 in the body lumen when the image was captured, etc. Metadata 173 may also include, for example, a validity indicator of the image. After checking several image parameters such as average brightness value and average color value, the image may be indicated as a valid image for processing and viewing, or as an invalid image (too dark, over-saturated, obstructed image or otherwise unfit for display). Metadata 173 may be captured, for example, during the time of capturing the image (e.g., along with the pixel data).

In one embodiment, review descriptor 174 may include user review data, such as data regarding one or more users' review process of the image. For example, review descriptor 174 may include one or more of the following indications: whether the image has been reviewed/displayed (yes/no indication), who reviewed the image (user/reviewer name), when the image was reviewed (date and time of review), the total accumulated display time that the image was presented to users, the number of users who studied the current image, etc. The data included in review descriptor 174 may be collected and stored, for example in receiver 112 and/or in processor 114. For example, when an image is displayed on a display unit of receiver 112, the review descriptor 174 associated with the displayed image may be updated with the date and time of display, and the viewer's name may be automatically or manually updated, for example, the viewer may be the patient undergoing the procedure, or the physician/nurse who is performing the procedure. Upon display of the image stream or portions of it after the procedure is completed, the user who is logged in to the workstation 117 may be automatically updated as the reviewer who studied the displayed images.

The review descriptor 174 may be created and associated with the image data 170 during the initial storage of the image in the receiving unit 112, during the time of capturing of the image by the in vivo device 140, during the download or compilation process of images from the receiving unit 112 to workstation 117 and/or after the download/compilation process. In another example, the image descriptor 174 may be created and associated to the image data 170 upon a first display of the image on a display device. Initially (for example before the set of images is first viewed), review descriptor 174 may receive a null, void or negative value, e.g., indicating that the image has not been reviewed or displayed to a user. The review descriptor 174 may be updated, e.g. upon display or after display of the image on a display device or monitor, to indicate that the image has already been viewed at least once.

In some embodiments, information describing review statistics of the movie may be stored with or associated with the movie. For example, a percentage of images out of the total (original) image stream which have been reviewed or displayed, a percentage of images out of a reduced image stream which have been reviewed or displayed, the number of reviewers who studied the current image stream, etc.

In some embodiments, descriptor data 172 does not necessarily include metadata 173 portion and analysis and classification data 175, and review descriptor 174 may include a minimal data structure. For example, review descriptor 174 may be a bit or a byte, e.g. as part of telemetry data of a stored image frame or associated with a stored image frame. The bit or byte may indicate whether the frame has been reviewed or has not been reviewed. Alternately, review descriptor 174 may be a data structure or a separate database, storing pointers or indexes to viewed and unviewed image frames.

Analysis and classification data 175 may be associated with the image data set 170, for example after image processing in receiver 112 and/or in processor 114. For example, a pathology detection algorithm may detect certain pathologies or abnormalities in the image, and accordingly the image may be classified as an image with, for example, suspected bleeding, suspected lesion, or suspected polyp. A body anatomy segment detector may classify the image according to the segment which it was captured in, e.g. an image from the small bowel, from the stomach, from the colon, or from the esophagus. More specific areas may also be determined, such as a duodenum image or a transverse colon image. Furthermore, similarity detection algorithms may classify the image as identical or substantially identical to a previous image. Other image processing algorithms may be used to analyze the image pixel data, for example contractions may be detected, e.g. as disclosed in U.S. patent application Ser. No. 12/282,700 titled "CASCADE ANALYSIS FOR INTESTINAL CONTRACTION DETECTION". Analysis/classification data 175 may also include information entered by the user. According to some embodiments the user may enter annotation information, such as a textual description or diagnosis of the image using, for example, a keyboard. The annotation may be stored as an entry in an annotation database, or as part of the image data e.g., the analysis/classification data 175.

Figure 2:
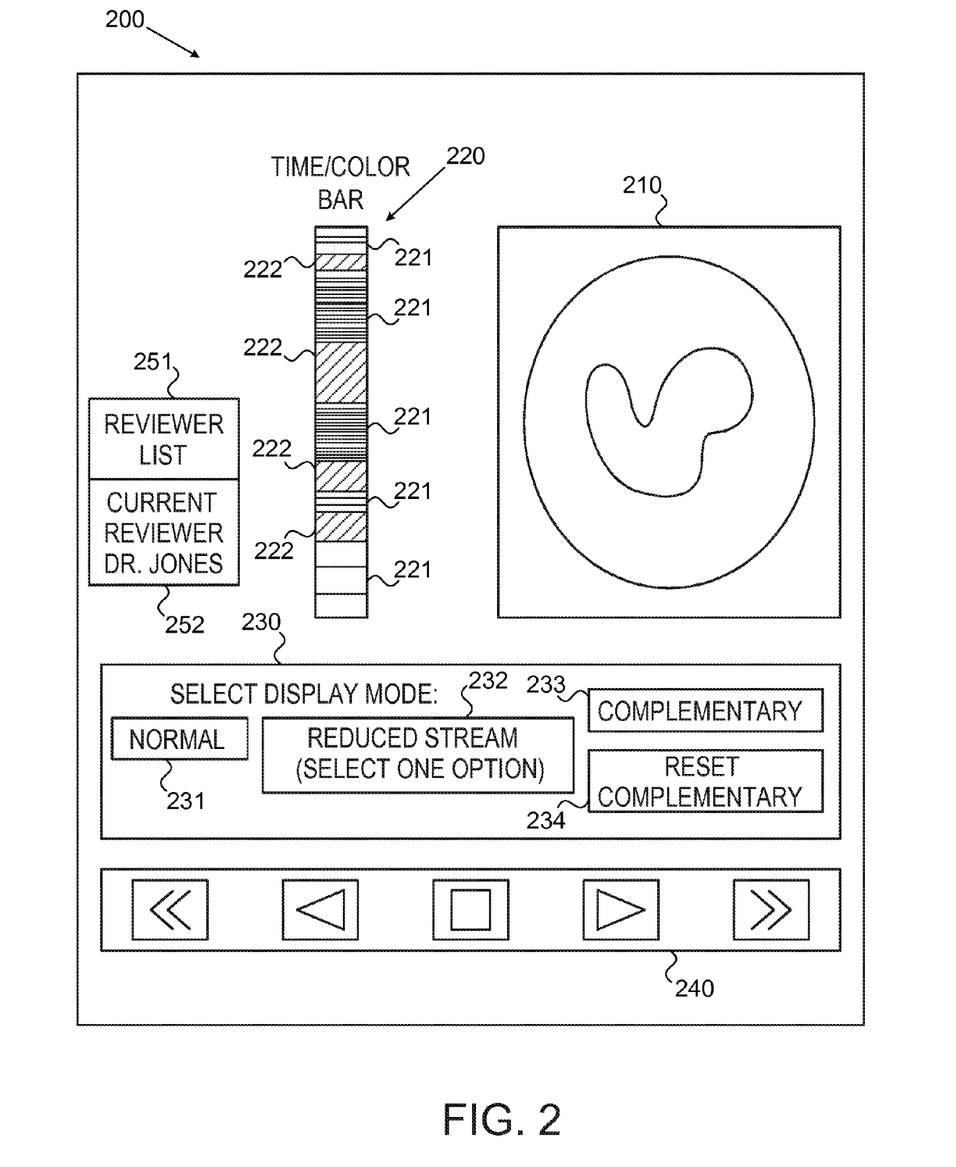
FIG. 2 is an exemplary graphical user interface including a set of user interface options and viewing tools displayed on a display or monitor according to an embodiment of the present invention.

Reference is now made to FIG. 2, which depicts a representation of an image and a control area displayed on the monitor 118 of FIG. 1A, according to one embodiment of the present invention. When viewing the image stream, according to one embodiment, the user is presented with several screen portions on monitor 118. An image portion 210 displays the image stream, or still images from the image stream. Graphical User Interface 200 may include control buttons 240 or other controls which may alter the display of the image; for example, stop, play, pause, capture image, step, fast-forward, rewind, or other controls. Such controls may be activated by, for example, a pointing device such as a mouse or trackball. Portion 230 may include a user interface for activating different display modes for viewing the captured images, for example a normal display mode 231, one or more reduced viewing modes 232, and one or more complementary modes 233.

According to one embodiment of the present invention, the user may switch from one viewing method to another while data is being streamed. A message window announcing/confirming the switch may be prompted, and the area and time frame of the resulting images may be displayed together with relevant details pertaining to the selected viewing method.

A user may select, for example using complementary view button 233 or another graphical user interface input method, to view only images which had not been reviewed previously. In some cases, a user may select to review specific images which had already been viewed by a previous user, for example a nurse may select to review only images which had been previously viewed by a specific professor. In another example, a reviewer may select to view a subset of images of the image stream which had not been previously reviewed, by one or more users. In some embodiments, the user can choose a specific person who previously reviewed one or more portions of the movie, and the user may review the images which have been viewed by that person, or alternatively may select to review only image which have not been reviewed by that person.

In some embodiments, each type of reduced image stream may have its corresponding complementary image stream, which may include all images from the original image stream which were not selected to be part of the reduced image stream. For example, the original set of images in stream may be denoted as group S, and the selected images in a first reduced image stream (e.g., a suspected bleeding indication image stream) may be denoted as subset $R_1$, wherein $S \supset R_1$. The complementary image stream $R_1^C$, corresponding to subset $R_1$, may be calculated as the relative complement, e.g. $S \backslash R_1 = R_1^C$.

Similarly, a different reduced image stream, e.g., a suspected polyp stream, may be denoted as subset $R_2$. The corresponding complementary image stream $C_2$ may be calculated as the relative complement, e.g. $S \backslash R_2 = R_2^C$ In any given point in time, the set of viewed images and the set of unviewed images are non-overlapping, e.g., there are no common images between the first displayed set and second displayed set. In some embodiments, images from the original stream may not be selected either for the first displayed set nor for the second displayed set, and a third complementary set may be generated for display. For example, in a reduced stream, certain images from the whole (original) set of images S captured by the in vivo device may be skipped. A first subset of images $I_1$ may include the group of images selected for display in the reduced stream R, and marked as viewed images after being viewed by a user. A second subset of images $I_2$, which does not include any of the images included in the first set $I_1$, may include images from the reduced stream which have not been reviewed yet, e.g. such that $I_1 \cup I_2 = R$. A third subset of images $I_3$ may include the images not selected for display in the reduced movie, e.g. such that $R \cup I_3 = S$. In some embodiments, the union of the three subsets is the original set of images captured by the in vivo device, e.g. $(I_1 \cup I_2) \cup I_3 = S$, and the intersection of each two subsets is an empty set (e.g. $I_1 \cap I_2 = \phi$, $I_2 \cap I_3 = \phi$ and $I_1 \cap I_3 = \phi$).

According to some embodiments, a time/color bar 220 or timeline portion may provide a timeline, an indication of the total time elapsed for the image stream, and may provide other information based on the selected viewing method, such as the total display time per image in the image stream, the percentage of frames that have been displayed out of the entire captured set of images, and other reviewer's session history, for example according to the selected viewing method. The timeline may be similar to, or may include, embodiments described in U.S. Pat. No. 7,215,338 titled "SYSTEM AND METHOD FOR PRESENTATION OF IN-VIVO DATA". For example, the timeline may include a color bar and/or a time bar, which may include a fixed display alongside the streaming display of the image stream. A cursor 223 or other indicator may move along the time/color bar 220 as the data stream is displayed and/or streamed so as to indicate to a health professional what part of the image stream is currently being displayed. The color content in the time/color bar 220 may map average colors of images in the data stream and give indication of the location of anatomical sites as well as possible locations of pathology. In an exemplary embodiment, the time/color bar 220 may be a bar labeled with time units, having different colors visually attached to the timeline at portions which indicate the time elapsed for the stream portions which are associated with image descriptors 172, or for the stream portions or images which have already been viewed. For example, cursor 223 may point to the relative location in the image stream of the current image being displayed in window portion 210. Time/color bar 220 may include portions 221, which may include unviewed images of the currently viewed stream. Portions 222 may indicate, for example in a single color e.g. black or gray, that images corresponding to these portions of the stream have already been viewed. In some embodiments, the color bar and timeline bar may be separated into two bars.

In some embodiments, portion 252 may include an indication of the current user who is reviewing the image stream. For example, the current user may be automatically updated as the user who is currently logged in to the workstation or review station, or the user may be manually updated by the user who is studying the image stream). Optionally, portion 251 may allow the reviewer to select one or more previous reviewers, from a list of previous reviewers, for example in order to complete review only portions of the image stream that they have not previously reviewed (by one or more users). After selecting the previous reviewer(s) using list 251 (e.g., a drop down list), the current reviewer may select viewing a complementary image stream using button 233. In other examples, the reviewer may want to view only images which have previously been viewed by a certain reviewer, for example a physician who referred a specific case to another physician in order to consult with him, or a patient who is seeking a second opinion regarding a diagnosis.

Portion 230 may include a selection of several buttons or controls of different display modes, which the user may use to switch between one viewing mode to another according to his/her preferred viewing routine. These buttons enable the user to easily toggle between viewing methods and switch, for example, from a summary view to its corresponding complementary view, or from a normal view to a summary view. The user can thus employ different viewing methods for different body areas imaged, or for different time segments of the image stream. A reset control button 234 may be provided to allow the user to reset or hide previous users' review data, and may allow the user to delete or reset the stored review history, for example by deleting or hiding a portion or all of the review descriptor 174 of one or more specific users. In one example, by selecting to reset the complementary mode, all previous users' review history may be hidden or deleted. In another example, the user may select to hide his/her own review history. Once reset button 234 is pressed, the presentation of different viewing modes may change accordingly. For example, the complementary image streams of one or more viewing modes (e.g., normal complementary mode, summary movie complementary mode) may not include any images, since the review history may be erased or hidden. In some embodiments, the list of reviewers may be updated, for example one or more users may be removed from the list.

A normal viewing mode 231 may include all images captured in the currently reviewed procedure. In another embodiment, normal viewing mode 231 may include a shortened stream of images, for example an image stream that includes merged images that are very similar to each other, or an image stream in which invalid images have been filtered out of (for example, images that are obscure, over-saturated, too dark, etc).

One or more reduced viewing modes 232 may enable a user to view a reduced image stream, for example based on editing methods as mentioned hereinabove. Images may be selected for a user to view based on one or more editing method. In some embodiments, a reduced viewing mode 232 may include images from the image stream which are suspected as abnormal images or images with pathologies. A reduced mode 232 may include the option of selecting a specific pathology and viewing only images which are suspected as relating to that pathology (e.g., images with suspected bleeding indication, images with suspected polyps, images with suspected Crohn's disease symptoms, etc).

In some embodiments, a reduced viewing mode 232 may include images which belong to a certain organ or to a specific segment of the imaging procedure, for example to a specific segment of the gastrointestinal tract such as the colon, the small bowel, the esophagus, the stomach, etc. In some embodiments, a user may select the percentage of image reduction in the reduced viewing mode 232, for example a user may select to view only 10% (or 25%, 33.3%, or any other percentage the user may choose) of the total number of images in the image stream, according to a specific criterion. For example, images in the stream may receive one or more scores according to predetermined criterions, for example a suspected pathology score, a bleeding indication score, a specific segment score that related the image to a segment of the imaging procedure, etc. According to one embodiment, images that received the highest score(s), according to the relevant scoring method (and/or editing method) selected by the user, may be displayed in the reduced viewing mode 232. In other examples, the "most clinically relevant" images may be automatically selected by one or more processors 114, 147, and/or 122, according to predetermined editing and selection methods.

The complementary or "unviewed" image stream may be defined by the set of images a user first views, or by an editing method first used, in that the unviewed images are the images not viewed by the user the first time and thus the images not selected by the user or the editing method.

One or more complementary viewing modes 233 may be calculated according to the previously selected viewing mode. For example, when a viewer uses a normal viewing mode 231, the corresponding complementary viewing mode 233 may include only images in the currently viewed stream which have not yet been reviewed by the viewer. In another example, when the viewer uses a reduced viewing mode, the corresponding complementary viewing mode 233 may include the rest of the images in the reduced stream which have not been reviewed yet. This embodiment may be advantageous and time-saving, for example when a physician first chooses to review a summary movie which includes 30 percent of the images in the original image stream, and then wants to review the rest of the image stream. Instead of viewing the complete (e.g. normal) view mode, which includes all images or substantially all images, the user may use the complementary mode to review only the remaining images (e.g., 70 percent of the original image stream), and thereby saves precious time.

Similarly, a viewer may select a complementary viewing mode 233 corresponding to one or more previous reviewers (which may be selected, for example, from list 251). In this embodiment, only images which have not been reviewed by at least one of the previous reviewers are displayed to the current reviewer. In some embodiments, a different control button 232 may be assigned to each different display method (e.g., button 232A for a summary movie, button 232B for a segment of the image stream for images from the colon only, button 232C for a bleeding indication portion of the image stream, etc). Similarly, a corresponding different control button 233 may be assigned to each display method (e.g. 233A for the complementary summary movie, 233B for all portions of the image stream except the colon, and 233C for all images not containing suspected bleeding indications).

In some embodiments, the review process may include a cyclic method, e.g. images may be reviewed by a user for example in normal mode or in a reduced/edited mode, the user may switch to a complementary mode and review new images, then click the complementary mode control button again to recalculate the current (updated) complementary viewing mode (e.g., remove images which have just been viewed from the set of unviewed images). In other embodiments, the complementary mode based on indication of unviewed images may be continuously updated, on-the-fly or substantially in real time. For example, each image being displayed may be immediately indicated as a viewed image upon its display on a monitor, and the processor may determine the complementary set of remaining (unviewed) images continuously while displaying the complementary view mode, such that the complementary mode always includes only images which have are indicated as unviewed.

The time/color bar 220 display may be adapted according to the selected viewing mode or method. For example, when a normal or reduced viewing modes are selected, the time/color bar 220 may show a fixed summary of colors of the image stream, for example as described in FIGS. 2-5 of U.S. Pat. No. 7,215,338 and/or in FIGS. 2-5 of Patent Application Publication Number 2007/0060798, which are incorporated herein by reference. When a complementary mode is selected, the time/color bar 220 display may be modified accordingly. For example, only stream portions 221 of bar 220 which correlate to the images that are part of the current view mode may be displayed. According to some embodiments, time/color bar 220 display may be changed according to the images which are part of the selected viewing mode. For example, in a reduced mode, or a user specific mode, the time/color bar 220 may display only portions 221 of the bar which correlate with the images which are part of the current view, and other portions of images 222 may be hidden. According to one embodiment, stream portions 222, which are not part of the current viewing mode, may be presented as black, grayed out, or hidden portions, in order to present clearly to the user that these portions are not part of the current view mode. This may enable quick differentiation between images in the current view and images which are displayed in the current view. According to embodiments of the present invention, portions 222 may represent portions of the image stream which have already been viewed by at least one user, or portions of the image stream which have not been viewed yet.

In some embodiments, the time/color bar 220 may be adapted according to the selected viewing mode. For example, if a user selects a summary view mode, the time/color bar 220 may be adapted to reflect the time and colors corresponding to the selected images of the summary view stream only. Instead of marking the image sections which are not displayed as hidden or black portions 222, a new time/color bar may be generated, based only on the selected images of the summary view mode and not taking into consideration the other images of the image stream. Similarly, a new color bar may be generated for each different viewing mode (reduced mode and/or complementary mode) of the image stream. The new color bar may replace the original time/color bar 220 which reflects the original image stream. In some embodiments, display methods may be combined, and the new color bar corresponding to a different viewing mode may be displayed in addition to the original color bar 220 which corresponds to the normal viewing mode.

The total number of images in the image stream may reach many thousands of images, for example 50,000 images. When selecting a normal viewing mode, bar 220 may include all images of the image stream. In one example, a user may view a few short sections of the image stream, then select a normal complementary viewing mode in order to view all images in the stream which have not been reviewed yet. However, since bar 220 may be a summarized representation of the image stream, a threshold of a number of viewed images may be determined, for example preset in advance or determined in real time, to calculate whether a pixel in the bar 220 should be presented as a black/hidden portion 222, or as a displayed portion 221. For example, the threshold may be determined based on the sequential number of images which have been viewed. In one example, if more than 300 sequential images have been viewed, the relative portion of bar 220 may be displayed as a black portion 222. In another example, the threshold may be determined based on a percentage of the number of viewed images out of the total number of images in the stream. If the total number of images in a reduced steam is 20,000, the threshold to display a black portion may be set, for example, to one percent of viewed images. Other methods of calculating the threshold for displaying black or hidden portions may be used.

In one embodiment, when viewing the image stream, a user may receive a graphic indication of which images had already been reviewed. The indication of viewed images may include for example displaying several patterns or colors. For example a different color may be assigned for each reviewer. The indication of viewed images may change according to the specific user who reviewed the image stream or a portion of it. In one example an image will be indicated as a "viewed image" or a displayed image if it had been reviewed by at least one user (e.g., any user). For example a first user may select to view an edited image stream, and afterwards a second user may select to view images of the same image stream which had not been reviewed yet by the first user. This may allow saving time, for doctors for example, who may select to view only a summarized portion of an image stream, while the rest of the image stream may be viewed by someone else, for example professional reviewers who may be situated in a local or remote review center. Moreover, if the images are stored in a network file, or in a file which may be accessed remotely, for example by more than one user simultaneously, one user may view a predetermined portion of the image stream (e.g., a reduced portion) while another user is viewing the complementary portion of the image stream.

The viewed images may be associated with or may include an indication or a review descriptor to indicate that they have already been viewed. The indication may include additional review information such as one or more reviewer's names, the time and date in which the images were viewed, the amount of time that the image was displayed on the screen, and/or other information which may be stored, for example automatically by a processing unit, during the review of an image stream by a user. The image information tag may be stored in a workstation, or on a network, for example in a dedicated database, or along with the stream image in an image database.

In one embodiment, images which have been indicated as viewed images may be displayed with a specific border, for example with a black or gray border or with no border at all. Images which are being displayed a first time may be indicated differently, for example by adding a color or otherwise different border (e.g., red, green, etc.) or by displaying a "new" icon near the image or at a corner of the image. Other methods of indicating viewed or displayed images may be used, for example the viewed images may be reduced in size or resolution. In another example, the display rate of unviewed images may be different from the display rate of viewed images. Images which have been indicated as viewed images may be displayed at a faster frame display rate, while unviewed images may be displayed at a slower display rate, i.e. remaining on display for a longer time.

Figure 3:
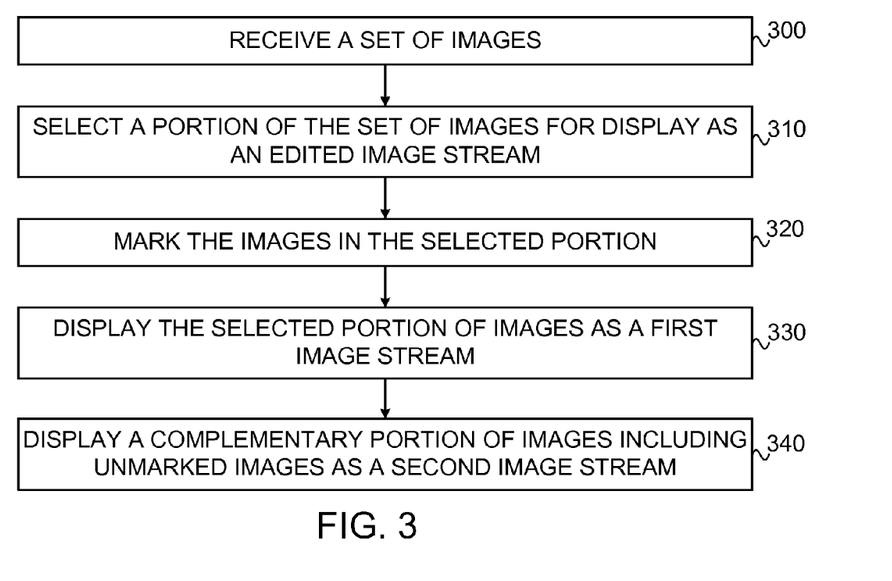
FIG. 3 is a flowchart of a method for displaying a complementary image stream according to an embodiment of the present invention.

Reference is now made to FIG. 3, which illustrates a method of providing a Graphical User Interface and displaying portions of an image stream according to embodiments of the present invention. While FIG. 3 is described with respect to embodiments shown in FIGS. 1-2, methods according to other embodiments of the invention may operate using different equipment. According to some embodiments, in operation 300, receiver 112 receives a stream of images, captured, for example by device 140. In operation 310 a portion of the image stream may undergo a selection or an editing process, which may include selecting a portion of the images for display as an edited image stream. The selection process may include any of the above mentioned editing methods or selection methods, e.g. analysis of the image for detecting pathologies and abnormalities in-vivo, analysis of the image to determine to which segment or organ of the body it belongs, etc.

According to some embodiments of the present invention, analysis of images from the stream of images, which can take place, for example, during a compilation process, may be performed by initiating one or more logical algorithms/methods, e.g. detection methods or algorithms for detecting 'interesting' images such as anomalous images. For example, according to some embodiments of the present invention, an algorithm may be used for detecting ulcers in-vivo, an algorithm may be used for bleeding detecting in-vivo and algorithm may used for detecting content in-vivo. In some embodiments each algorithm may include one or more algorithms for detecting several types of in-vivo abnormalities, such as types of ulcer, bleeding etc. Other algorithms may detect to which segment of the imaged body lumen the image belongs, or may detect other abnormalities in the images.

A value or weight may be set for the detection results of each algorithm, for determining the relevance and importance of the abnormality or result detected by the algorithm. For example, for images in which intestinal content was detected, a negative value may be assigned, since usually images with high content level are unclear and will not supply enough clear information that can be of use, for example to a physician reviewing the lumen imaging results. Images of internal bleeding or ulcers, on the other hand, may be assigned a high positive value as these may be of special interest for the physician or expert reviewing these results. Integration of the detection results generated by each algorithm may be performed, for example by an integrator algorithm, for each image. As a result, an image containing, for example abnormalities such as bleeding or ulcers will generate a relatively high final value, whereas an image showing, for example over 90% content will generate a relatively low value. A final score may be calculated for each image, and the scores from each detection algorithm may be stored and used according to the selected viewing method.

In operation 320, the images in the selected portion may be marked, tagged or classified as belonging to one or more predetermined sets of images. For example, processor 114 and/or processing unit 122 may operate certain classification and/or detection algorithms and may change descriptor data 172 of one or more images, to indicate those images as belonging to one or more specific subsets or groups of images. Such indication may be stored in metadata 173, in analysis and classification data 175, and/or in other data structures which may be associated to the images. The sets of images may be predetermined, and/or may be selected and/or configured by a user. In some embodiments, the sets of images may be automatically determined by the processor 114, for example upon detection of an image as belonging to a specific set, the specific set may become available to the user (e.g. through the Graphical User Interface) for selection of the set as a viewing mode. Sets of images may include, but are not limited to, images belonging to a specific segment or organ of the body, images suspected as containing one or more detected pathologies, etc. The indication of an image belonging to one or more certain sets of images may be performed by setting a bit in an existing data structure associated with the image, and/or by adding a descriptor and associating it with the image. Optionally, lists of images may be created to indicate the images as belonging to a specific group (e.g., the image frame number or serial number or a pointer to the image frame may be added to one or more lists which may store all images classified as belonging to a certain group).

When one or more classification/detection procedures is completed, selected images may be marked as belonging to one or more predetermined sets of images, each set being a subset of the complete set of images captured by the in vivo device. A complementary set of images may be created, for example for each subset of images the complementary set of images may be determined by calculating the relative complement of the subset and the complete set of images. Such complementary streams may be created upon the creation of the subsets of images, and/or later on, for example upon demand of a user to view a certain complementary set.

In operation 330 an edited movie, e.g. a movie which includes images that received the highest scores for a selected viewing mode or classification algorithm, may be generated for example by processor 114 for display on monitor 118. The generation of the reduced/edited movie may be performed in advance, for example during download and/or compilation of the images from the image stream, or in real time, for example upon a user's selection of a specific viewing mode. A Graphical User Interface such as display portion 230 is provided to the user, and upon the user's selection of the viewing mode, the selected edited movie is displayed as an image stream, for example along with relevant user options such as fast-forward, back, skip portion, stop, and pause. In other embodiments, a complementary view may be created based on frames un-viewed due to a user pausing, stopping, or skipping images within a displayed stream. Thus certain operations (e.g., creating an edited image stream) need not be used. In some embodiments, both options may be combined, e.g. the complementary movie may be calculated by including the images not selected for the edited movie, and images which have been skipped/unviewed by the user in the edited movie. Other combinations are possible.

In operation 340 a complementary view of the edited movie is presented to the user. The complementary stream may be calculated in advance, e.g., when the images are selected for the edited movie, the unselected images from the original image stream may be stored as the complementary movie of the specific viewing mode. In another embodiment, for example if the edited movie is generated by the processor 114 upon a user's selection of a specific viewing mode, the complementary movie may also be generated on-the-fly, for example by eliminating images in the selected viewing mode from the images in the original stream. In another example, a summary movie may be generated upon compilation of the raw data stream received in workstation 117, and the corresponding complementary movie may be generated substantially immediately thereafter. For example, every image which is selected as part of the summary movie is tagged, or associated with an image descriptor 172 which indicates it belongs to the set of summary movie images (e.g. operation 320). Other images in the image stream may remain untagged, or may receive another indication in their corresponding image descriptor 172 (e.g., in metadata 173 or in analysis/classification data 175) that specifies these images are not part of the summary image stream.

When generating a complementary image stream, a relevant data structure associated with all images in the stream may be scanned, and only images which have not been marked or otherwise indicated as summary movie images, may be placed in the complementary stream. In another example, the reduced stream and its corresponding complementary stream may be generated based on a specific threshold value. In this embodiment, each image receives a score or a value based on detection algorithms as mentioned above. The score or value may be stored in association with the image stream, for example in storage unit 119 or 125. The score may be assigned to the images during a processing operation performed on all images arriving from the in vivo device (e.g., a detection/classification algorithm), and may be performed in the receiving unit 112 and/or in the processor 114.

The summary stream may be generated, for example using all images that receive a score higher than a predetermined threshold value, or by selecting for example the top 10% of images which received the highest score. A complementary image stream may be generated based on the remaining images in the stream, e.g. the images that receive a score which is lower than or equal to the threshold value, or 90% of images which received the lowest score. Different complementary streams may be generated per each reduced image stream. In another example, images may be classified to belong to a certain segment of the imaged body lumen. According to the user's selection, only images pertaining to a selected segment (e.g., the small bowel or the colon) may be displayed in one embodiment. The complementary image stream may include all images which are not classified as belonging to the selected segment.

The complementary view of the summary movie may include all images from the original images stream which are not part of the summary movie. Thus, a physician or professional reviewer may select to watch the automatically generated summary movie first, and then watch the complementary image stream, to review the rest of the images in the stream and ensure nothing was missed by the detection algorithms. Similarly, a physician may view a certain portion of the image stream, e.g. a suspected pathology stream, and may ask a professional reviewer to review the rest of the images from the original (or full) stream, e.g. the corresponding complementary image stream. A Graphical User Interface may include a button to display the summary movie, and another button to display the complementary summary view movie. In some embodiments, a complementary view corresponding to a certain viewing mode may be generated for one or more viewing modes provided in the user interface and displayed, for example, on display 118.

In some embodiments, the Graphical User Interface may include a time/color bar 220 corresponding to the selected complementary view mode, as described in FIG. 2. A user may select one or more images viewed and associate annotations or diagnosis to these images. Time/color bar 220 may be separated into two or more separate bars, which may provide a timeline, and may include for example summaries of annotations, with reference to the appropriate relative time of the image on the time chart based on the selected viewing method.

Figure 4:
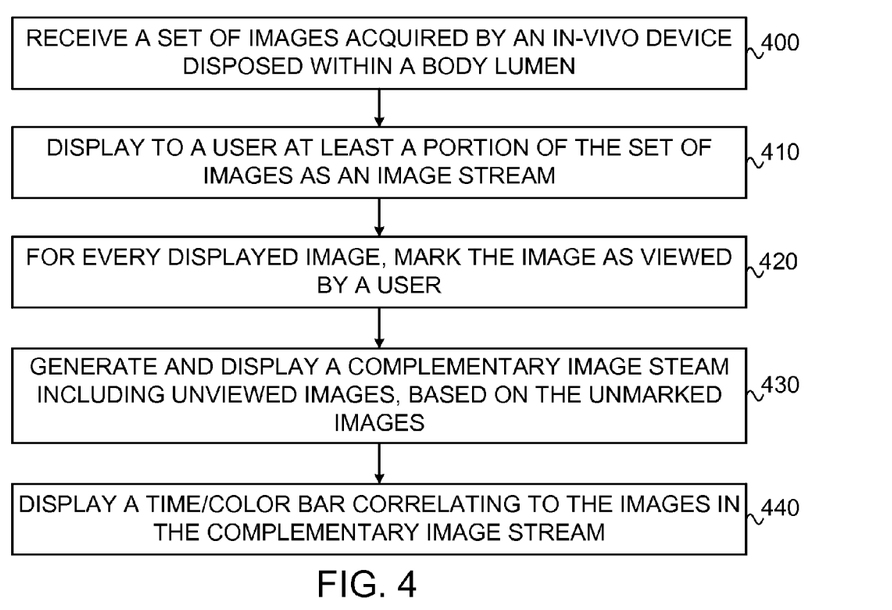
FIG. 4 is a flowchart of another method for displaying a complementary image stream, according to an embodiment of the present invention.

FIG. 4 depicts a flowchart for generating and displaying a complementary image stream, according to embodiments of the present invention. In operation 400 a set of in vivo images captured by imaging device 140 are received by workstation 117 from receiving unit 112. The set of images are stored, for example, in storage unit 119. According to some embodiments, the image stream may be edited according to various criteria (one or more), such that different portions of the image stream may be included in different viewing modes which may be selected by a user (such as normal viewing mode, summary viewing mode, selected pathology viewing mode, GI segment viewing mode, etc). The edited image streams for display in different viewing modes may be stored, for example in storage unit 119, or in a separate or remote storage unit.

In operation 410 the user interface may provide one or more optional viewing modes which a user may choose from. Such viewing modes may be selected by the user choosing one mode from a selection box, or by pressing a button (e.g., using a pointing device or keyboard) or a control which relates to the wanted viewing mode. Upon selection of a viewing mode by a user, the corresponding image stream may be displayed, for example on display 118 or on a separate monitor which may be connected, for example by wired or wireless network, to the storage unit 119. The different image streams corresponding to the different viewing modes may be generated in advance by processor 114 and stored, for example in storage unit 119, or may be generated in real time, for example after the user selects the viewing mode. In some embodiments, the image stream generation methods may be combined, e.g. a portion of the images may be filtered out in the receiver 112, e.g. immediately after recording an image, and another portion may be filtered out by processor 114 upon display or selection of a certain viewing method.

In some embodiments, the information regarding which image belongs to a certain viewing mode may be stored as part of the image descriptor data 172, e.g. in analysis/classification data 175. In such embodiments, only a single stream may be stored in the storage unit in order to save storage space and eliminate the need to store duplicate images, since a single image may be a part of several edited image streams or several viewing modes. For example, the image data 170 may include list with entries of all possible viewing modes, and each entry may receive a positive value if the particular image is a part of the viewing mode, or a negative or null value if the image is not to be displayed when that viewing mode is selected. Other implementation methods may be applied as known in the art.

A user may select a viewing mode from, for example, the viewing modes and editing methods mentioned hereinabove, e.g. normal viewing mode, reduced viewing mode (e.g. summary movie), pathology viewing mode, gastrointestinal (GI) segment viewing mode, etc. Each mode may have several viewing options related to it that the user may choose from.

For example, in the GI segment viewing mode, the user may select the segment he/she wishes to view, or the processor (e.g. processor 114) may automatically select or suggest the segment for review based on the type of procedure that the patient underwent or based on analysis and classification of the images.

In operation 420, a processor, e.g. processor 114 or processor 122, may mark the image as a "viewed" image. For example, processor 114 may associate a review descriptor 174 with images which have been viewed by a user. This may be performed, for example, upon the display of each image on a monitor or display unit 118. The review descriptor 174 may include data such as the image serial number and/or time stamp, the user (or list of users) who reviewed the image, the time and date of displaying the image, the total time that the image was displayed on screen, etc. In some embodiments, a review descriptor 174 may be assigned to every image, and may be stored along with the pixel data in receiver 112, or in storage unit 119. The review descriptor 174 may contain an indication whether the image had been displayed to at least one user.

In operation 430, a complementary image stream may be generated. The complementary image stream may include only images from the original images stream which are indicated as not viewed yet, or images which are associated with, for example, a null or void review descriptor 174. Generation of the complementary image stream may include selecting, for example by a processor 114 operationally connected to display 118, images from an image stream which were not displayed yet to a user. The image stream may be the original image stream acquired by the device 140, or an edited image stream (e.g., an image stream which includes a portion of selected images from the original stream). A graphical user interface may allow the user to select between one or more complementary viewing options, which may be based on the current viewing mode used. For example, a user may select to view:

a complementary image stream which includes images from the original (full) image stream which have not been viewed yet (e.g., indicated as unviewed based on review descriptor 174);
  a reduced complementary image stream which includes only images from a reduced image stream (e.g., images from a summary movie) which have not been displayed yet;
  or other streams. In some embodiments, the complementary image stream may be calculated or created based on a user's selection of reviewers from a list of reviewers. For example, suppose stream X has been partially reviewed by users B, C, D and E. User A may select to view only images which have been reviewed by users B and C (e.g., view a reduced image stream). In another example, user A may select to view a reduced complementary image stream, e.g. only images which have not been reviewed by users B and C. In this example, although the image stream was reviewed by other users as well, users D and E, the review descriptor 174 may include, for each image or for each reviewed image, review history information detailing which user reviewed it. Based on the review descriptor 174, the requested reduced complementary image stream may be calculated, for example by processor 114 or by a different processor which may be operationally coupled to a display unit and to the image data storage unit, e.g. storage unit 119.

In operation 440, a time/color bar, e.g. time/color bar 220, may be displayed to a user, in correlation to the complementary image stream which is displayed and alongside it. For example, the time/color bar may hide or mark images which were eliminated from the complementary movie (e.g. images which have already been reviewed, or images which were part of the summary movie). The time/color bar may be updated during the display of images, presenting to the user which portion of the image stream currently viewed (e.g. original or reduced) has already been reviewed. In some embodiments, the user may define specific parameters which may be stored for that user and used whenever he is logged in to the workstation, for example a user may determine a group of users he considers relevant, who should be taken in to consideration when calculating the complementary image stream based on selected reviewers.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

The invention claimed is:

1. A method for displaying an image stream, the method comprising:
  receiving a set of images acquired by an in-vivo device disposed within a body lumen;
  displaying a bar indicating which images of the set of images have been displayed to the user and which images of the set of images which have not been displayed to the user;
  selecting a portion of the set of images using an editing method;
  displaying to a user on a monitor the selected portion of the set of images as an image stream displayed as a movie;
  associating, using a processor, a review descriptor with every image of the selected portion of the set of images which has been displayed, the review descriptor including at least an indication that the image has been displayed to a user; and
  modifying the bar to correspond to only the images of the selected portion of the set of images, the modified bar indicating which images of the selected portion of the set of images have been displayed to the user and which images of the selected portion of the set of images have not been displayed to the user, according to the review descriptors.

2. The method of claim 1, comprising: associating a review descriptor with each image.

3. The method of claim 1, comprising: providing a graphical user interface to select a display method.

4. The method of claim 3, wherein the display method is selected from: viewing a portion of images from the image stream, wherein said images are indicated as unviewed, viewing all images of the image stream, and viewing a summarized portion of the image stream.

5. The method of claim 1, wherein the device is a swallowable capsule.

6. The method of claim 1, wherein the images are from a gastrointestinal tract.

7. The method of claim 1 comprising calculating the complementary set of images substantially upon a request of a user to view the complementary image stream.

8. The method of claim 1 comprising hiding one or more previous users' review history.

9. The method of claim 1, wherein the review descriptor comprises data selected from the group comprising: the user that reviewed the image; when the images was reviewed; the total accumulated display time that the image was presented; and the number of users who viewed the image.

10. The method of claim 1, wherein the bar comprises a fixed display and a cursor, the cursor to move along the time bar to indicate the portion of the image stream being displayed.

11. A system for displaying a complementary view of an image stream, the system comprising:
- a storage unit for storing a set of images acquired by an in-vivo device;
- a processor to:
  - display a bar indicating which images of the set of images have been displayed to the user and which images of the set of images have not been displayed to the user;
  - select a portion of the set of images for display using an editing method;
  - display to a user the selected portion of the set of images as an image stream displayed as a movie;
  - associate a review descriptor with every image of the selected portion of the set of images which has been displayed, the review descriptor including at least an indication that the image has been displayed to a user; and
  - modify the bar to correspond to only the images of the selected portion of the set of images, the modified bar indicating which images of the selected portion of the set of images have been displayed to the user and which images of the selected portion of the set of images have not been displayed to the user, according to the review descriptors; and
- a storage unit to store the review descriptors.

12. The system of claim 11 wherein the display unit is for displaying the image stream or portions thereof.

13. The system of claim 11 comprising a graphical user interface for selecting a viewing mode.

14. The system of claim 13 comprising a control for selecting a viewing mode based on one or more previous users' review history.

15. The system of claim 10 wherein the processor is to indicate an image as a viewed image upon initial display of the image on the display unit or substantially immediately thereafter.

16. A system for displaying portions of an image stream, the system comprising:
- a storage unit for storing images acquired by an in-vivo device;
- a processor to:
  - select images for display according to a viewing mode;
  - generate a first image stream from the selected images, and a second image stream from unselected images; and
  - create and associate a review descriptor to one or more images, the review descriptor including at least an indication if the one or more images have been viewed by a user;
- a display for displaying the first and second image streams as movies and for displaying a bar indicating which images of the set of images have been displayed to the user and which images of the set of images which have not been displayed to the user, according to the review descriptors; and
- a storage unit to store the review descriptors;
- wherein the display is to modify the bar according to the viewing mode.

17. The system of claim 16 comprising a graphical user interface for selecting images for display according to one or more criteria.

18. The system of claim 16 comprising a graphical user interface for selecting images for display according to one or more previous users' review history.

19. The system of claim 16 wherein the processor is to indicate an image as a viewed image upon initial display of the image on the display unit or substantially immediately thereafter.

* * * * *